United States Patent
Hara et al.

(10) Patent No.: US 6,656,502 B1
(45) Date of Patent: *Dec. 2, 2003

(54) SUSTAINED-RELEASE PROSTAGLANDIN I DERIVATIVE PREPARATION

(75) Inventors: Michio Hara, Kawasaki (JP); Yasuhide Horiuchi, Kamakura (JP); Fuminori Tamura, Mishima (JP); Keishi Yamasaki, Kamakura (JP)

(73) Assignee: Toray Industries, Inc., Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/180,757

(22) PCT Filed: Mar. 13, 1998

(86) PCT No.: PCT/JP98/01057

§ 371 (c)(1),
(2), (4) Date: Jan. 12, 1999

(87) PCT Pub. No.: WO98/41210

PCT Pub. Date: Sep. 24, 1998

(30) Foreign Application Priority Data

Mar. 14, 1997 (JP) .................................... 9/61501

(51) Int. Cl.⁷ ............................. A61K 9/20; A61K 9/22
(52) U.S. Cl. ..................... 424/464; 424/480; 424/486; 424/488; 424/468; 514/944; 514/468
(58) Field of Search .................................. 514/468, 944; 424/400, 464, 468, 474, 480, 486, 488

(56) References Cited

U.S. PATENT DOCUMENTS 5,232,704 A * 8/1993 Franz et al. ................. 424/456

FOREIGN PATENT DOCUMENTS

| JP | A 58-124778 | 7/1983 |
| JP | A 62-77335 | 4/1987 |
| JP | A 2-218621 | 7/1990 |
| JP | A 2-225416 | 9/1990 |
| JP | 2225416 | * 9/1990 |
| JP | A 4-74137 | 3/1992 |

OTHER PUBLICATIONS

Sadao Iguchi et al., "New Drug Development System Synthetic Technology, Base and Additives (in Japanese)", Tokyo: R&D Planning, Jul. 12, 1985, p. 429–436.

* cited by examiner

Primary Examiner—Lakshmi Channavajjala
(74) Attorney, Agent, or Firm—Birch Stewart Kolasch & Birch LLP

(57) ABSTRACT

A sustained release preparation of prostaglandin I derivatives, which is highly safe and has stable drug-releasing and absorption properties, is disclosed. In the orally administrable preparation, the active component is a prostaglandin I derivative and the release-controlling component is a hydrogel base.

4 Claims, 20 Drawing Sheets

SUSTAINED-RELEASE PROSTAGLANDIN I DERIVATIVE PREPARATION

This application is the national phase under 35 U.S.C. §371 of prior PCT International Application No. PCT/JP98/01057 which has an International filing date of Mar. 13, 1998 which designated the United States of America, the entire contents of which are hereby incorporated by reference.

TECHNICAL FIELD

The present invention relates to a sustained release preparation of prostaglandin I derivatives, which comprises a prostaglandin I derivative as an active component, which controls the release of the prostaglandin I derivative from the preparation so as to exhibit stable sustained release of the derivative.

BACKGROUND ART

Prostaglandin I (hereinafter referred to as "PGI" for short) has a strong inhibition action of agglutination of platelets and strong vasodilator action, and is used for various diseases such as peripheral circulatory disturbance. It has been discovered that some of the compounds have anti-ulcer actions and their pharmacological effects thereof are wide.

On the other hand, studies of sustained release preparations are now intensively made for other drugs too. Especially, studies are made for the purpose of giving sustained effect to drugs of which biological half lives after administration are short; decreasing side effects of drugs which likely exhibit side effects $C_{max}$-dependently; and improving compliance by decreasing the number of times of administration.

General means for attaining sustained release include sustained release hydrogel preparations (Int. J. Pharm., 15(1983)25–35) using water-soluble polymers as sustained releasing bases; sustained release matrix preparations using hydrophobic polymers; and sustained release granules using hydrophobic coats; and a method for sustained release suited for the particular drug is employed.

Prostaglandins including PGI are generally chemically unstable and their biological half lives are very short, so that frequent administration per day is required for usual preparations (preparations for injection, rapid-releasing oral administration and for topical application) in order to sustain the pharmacological effects. Thus, research and development of sustained release preparations of prostaglandins are now intensively made for injection and topical application for the purpose of sustaining pharmacological effects, reducing side effects, improving compliance and the like. Examples of the developed sustained release preparations include a sustained release preparation of PGI in which PGI is dispersed in an anti-thrombogenic material disclosed in Japanese Laid-open Patent Application (Kokai) No. 1-280466; sustained release injections by encapsulating PGE1 or PGI in liposomes (Prostaglandins, 33 (1987) 161–168); sustained release preparations of PGEs for eye drops for the purpose of topical application (Laid-open Patent Application (Kokai) No. 4-253910); sustained release preparations for intrauterine application (Japanese Laid-open Patent Application (Kokai) No. 55-102512, Br. J. Obstet. Gynaecol., 99 (1992) 877–880); preparations to be applied to buccal mucosa (Laid-open Patent Application (Kokai) No. 59-48409); and preparations to be applied to skin (Arzneim.-Forsch./Drug Res., 43 (1993) 450–454).

However, as for preparations of prostaglandins including PGI derivatives for oral administration, satisfactory sustainment of release is not necessarily attained because of the problems in chemical stability and stability of release of the drug in gastrointestinal tract. For example, in cases where a hydrophobic sustained releasing base such as ethyl cellulose is used, since the contents of PGI derivatives in the preparations are very small, the release of the drug from the preparation is poor because of the absorption to the base, the bioavailability is decreased because of the sustained release, influence by food is increased, and the releasing property is changed when the preparation is stored for a long time (Prostaglandins, 41 (1991) 473–486). Further, since the PGI derivatives have very strong pharmacological activities and trace amount thereof exhibits pharmacological effects and side effects, more precise control of the amount of the released drug is necessary than in the case of other drugs, for the sustained expression of the pharmacological effects and for avoiding side effects. However, the release rate of an orally administered drug fluctuates due to pH change in the gastrointestinal tract, and the distributions of the blood levels between individuals or in an individual tend to be large. Because of these problems, it is desired to provide an orally administered sustained release preparation which has a high safety, and exhibits stable release and absorption of the drug.

DISCLOSURE OF THE INVENTION

Accordingly, an object of the present invention is to provide a sustained release preparation of prostaglandin I derivatives which has a high safety, and exhibits stable release and absorption of the drug.

The present inventors intensively studied for attaining the above-mentioned object to discover that a sustained release preparation which has high stability (pH stability, storing stability and the like) of release of the trace amount of PGI derivative, and which gives a high bioavailability (complete release of the drug), is attained by selecting hydrogel base as the release-controlling component, thereby completing the present invention.

That is, the present invention provides an orally administrable sustained release preparation of prostaglandin I derivatives comprising an effective component and a release-controlling component, wherein the effective component is a prostaglandin I derivative and the release-controlling component is a hydrogel base.

The oral sustained release preparation of PGI according to the present invention exhibits high stability of the release of PGI and high bioavailability, and is a very preferred sustained preparation for sustained release of a drug in the gastrointestinal tract as will be concretely shown in the examples below. The preparation also exhibits pH-independent release of PGI by adding a buffer agent. As will be apparent from the oral absorption test described below, it was proved that a prescribed blood level of the drug is maintained for a long time by using the oral sustained release preparation according to the present invention. This suggests a possibility of sustainment of the pharmacological effects and reduction of side effects. Thus, the preparation is expected to be used as a sustained release preparation having high safety and effectivity for therapies of various diseases.

BEST MODE FOR CARRYING OUT THE INVENTION

Figure 1:
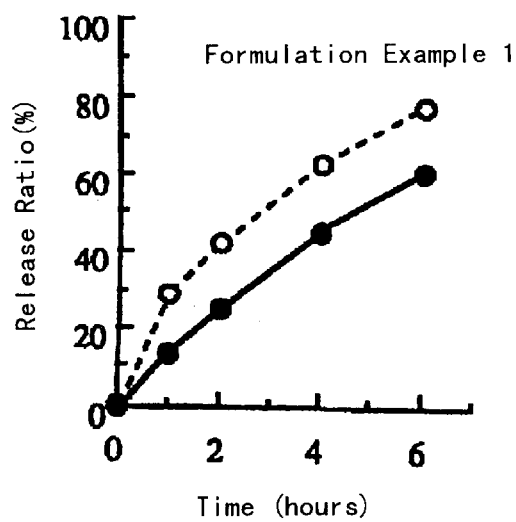
FIG. 1 is a graph showing the release profiles of the drug from the tablet obtained in Formulation Example 1.
Figure 2:
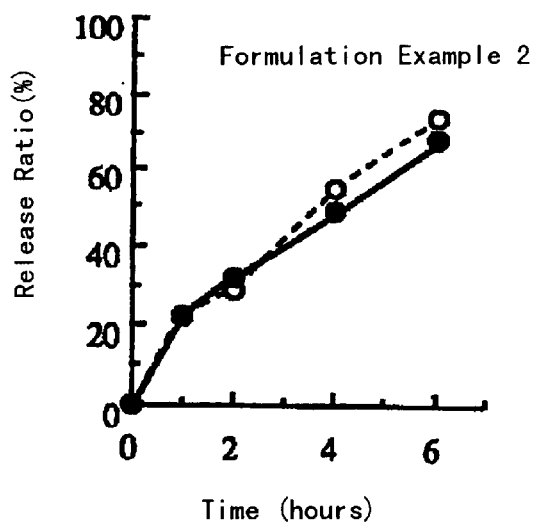
FIG. 2 is a graph showing the release profiles of the drug from the tablet obtained in Formulation Example 2.
Figure 3:
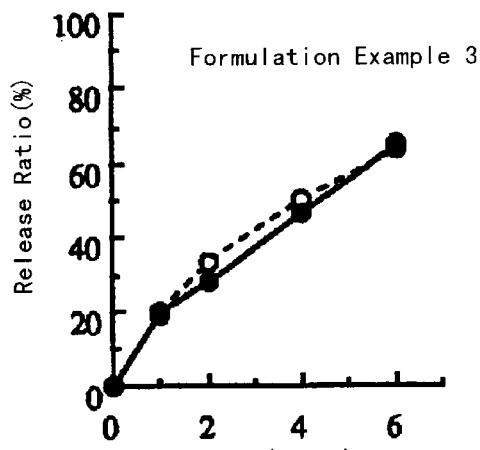
FIG. 3 is a graph showing the release profiles of the drug from the tablet obtained in Formulation Example 3.
Figure 4:
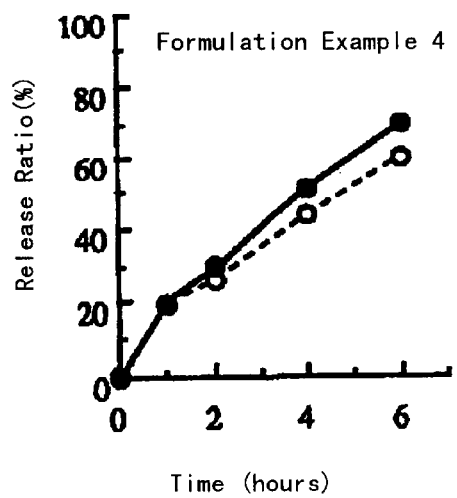
FIG. 4 is a graph showing the release profiles of the drug from the tablet obtained in Formulation Example 4.
Figure 5:
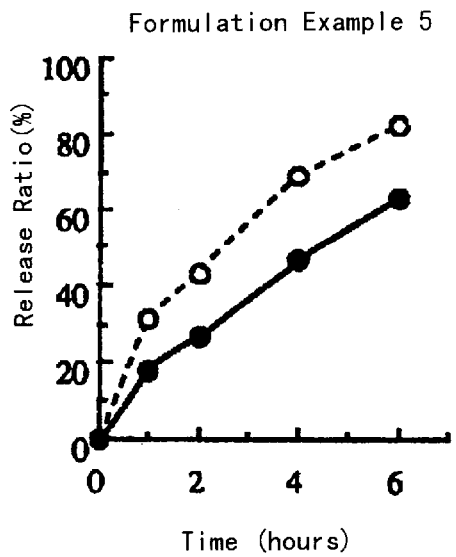
FIG. 5 is a graph showing the release profiles of the drug from the tablet obtained in Formulation Example 5.
Figure 6:
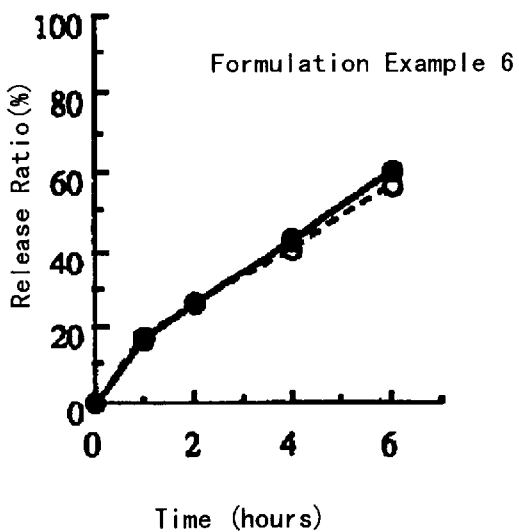
FIG. 6 is a graph showing the release profiles of the drug from the tablet obtained in Formulation Example 6.
Figure 7:
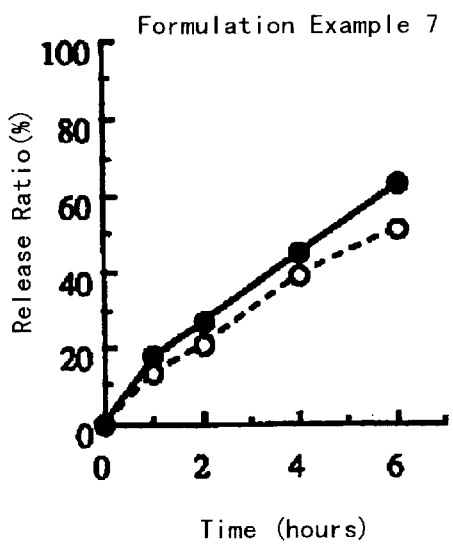
FIG. 7 is a graph showing the release profiles of the drug from the tablet obtained in Formulation Example 7.
Figure 8:
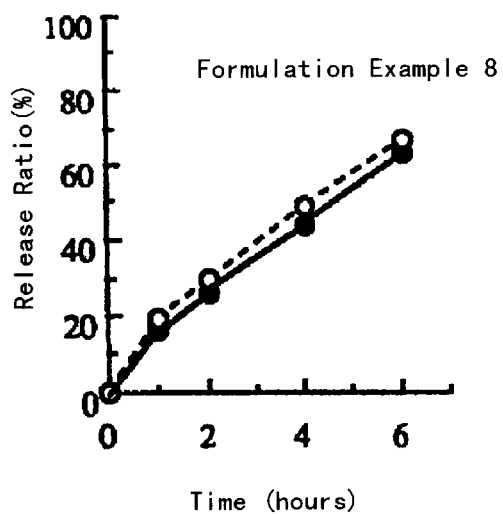
FIG. 8 is a graph showing the release profiles of the drug from the tablet obtained in Formulation Example 8.
Figure 9:
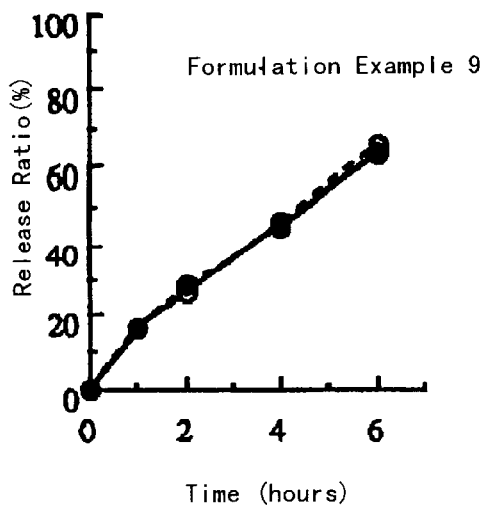
FIG. 9 is a graph showing the release profiles of the drug from the tablet obtained in Formulation Example 9.
Figure 10:
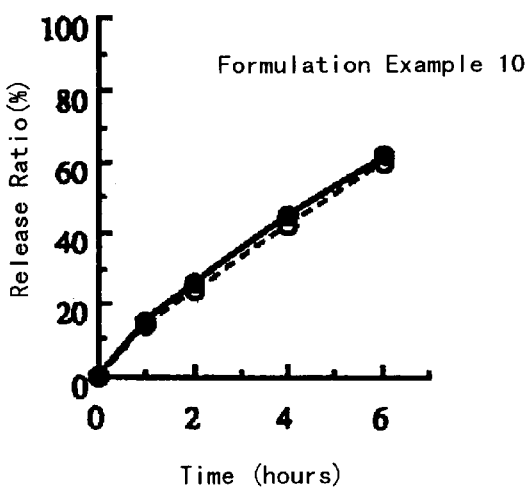
FIG. 10 is a graph showing the. release profiles of the drug from the tablet obtained in Formulation Example 10.
Figure 11:
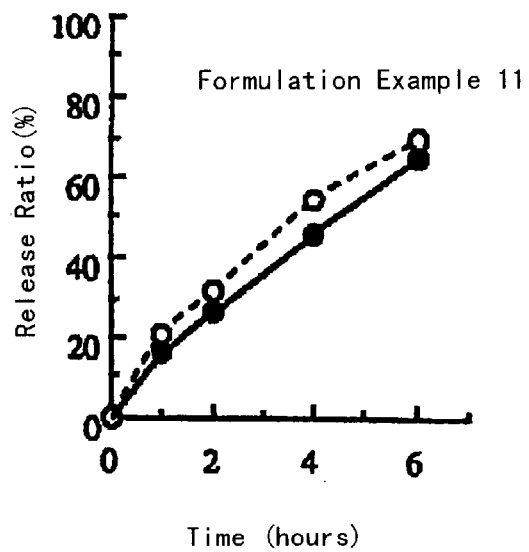
FIG. 11 is a graph showing the release profiles of the drug from the tablet obtained in Formulation Example 11.
Figure 12:
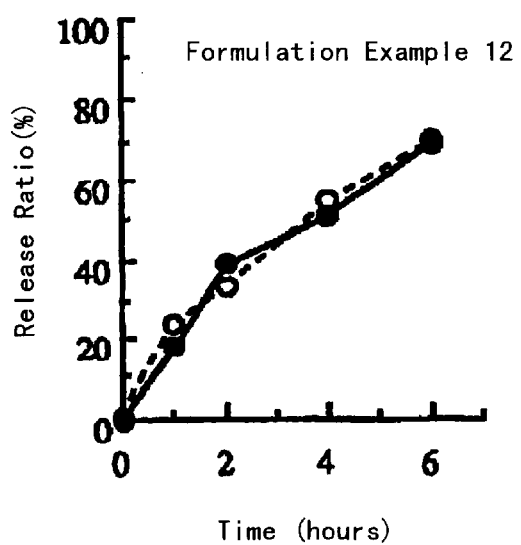
FIG. 12 is a graph showing the release profiles of the drug from the tablet obtained in Formulation Example 12.
Figure 13:
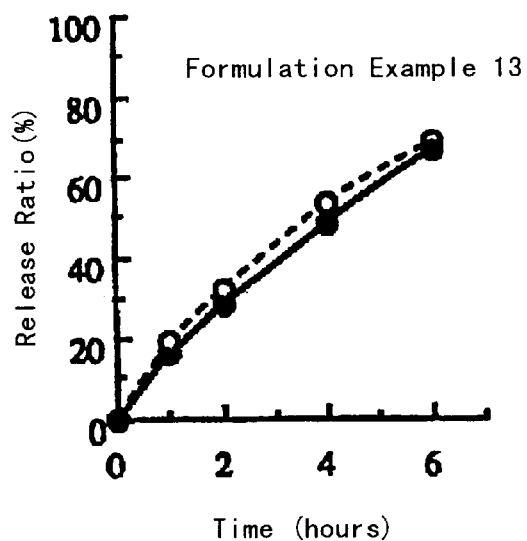
FIG. 13 is a graph showing the release profiles of the drug from the tablet obtained in Formulation Example 13.
Figure 14:
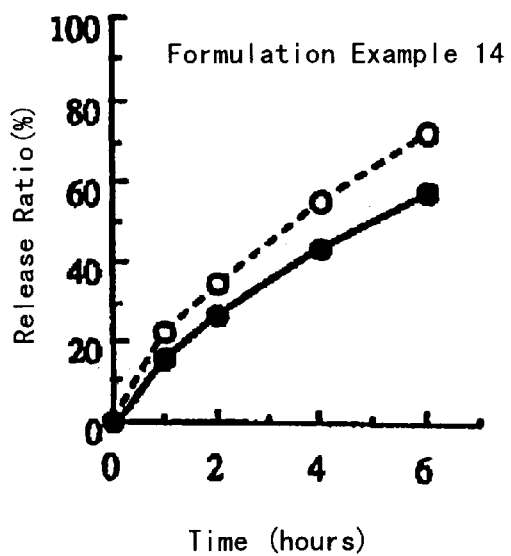
FIG. 14 is a graph showing the release profiles of the drug from the tablet obtained in Formulation Example 14.
Figure 15:
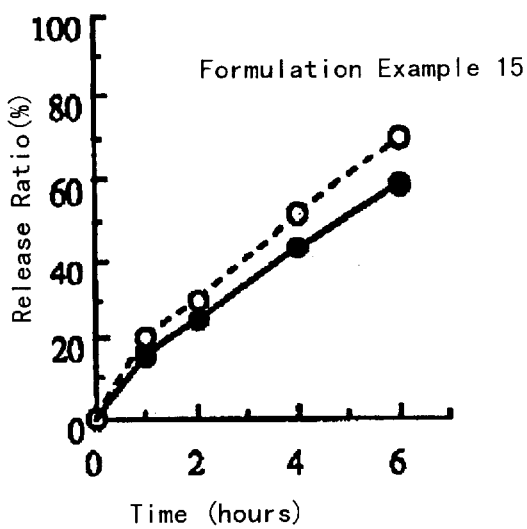
FIG. 15 is a graph showing the release profiles of the drug from the tablet obtained in Formulation Example 15.
Figure 16:
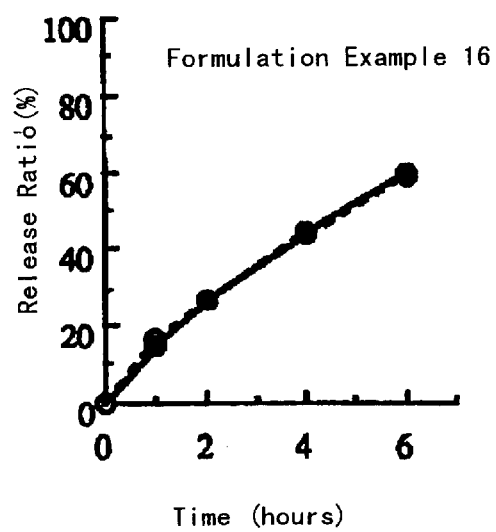
FIG. 16 is a graph showing the release profiles of the drug from the tablet obtained in Formulation Example 16.
Figure 17:
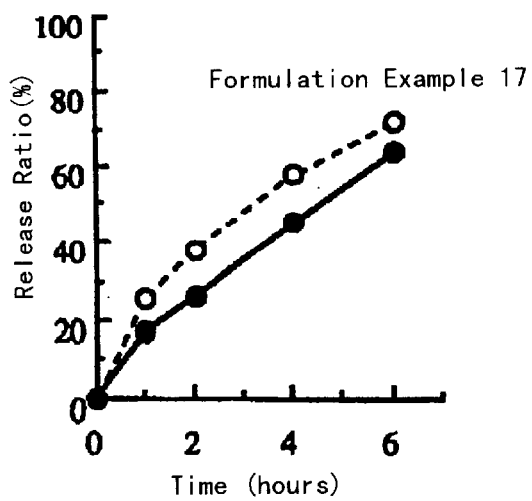
FIG. 17 is a graph showing the release profiles of the drug from the tablet obtained in Formulation Example 17.
Figure 18:
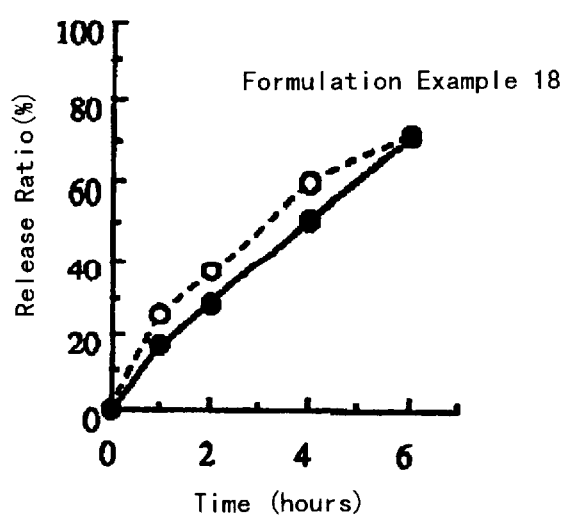
FIG. 18 is a graph showing the release profiles of the drug from the tablet obtained in Formulation Example 18.
Figure 19:
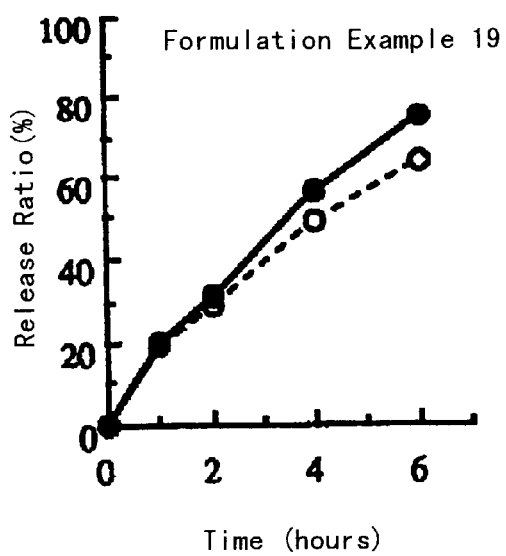
FIG. 19 is a graph showing the release profiles of the drug from the tablet obtained in Formulation Example 19.
Figure 20:
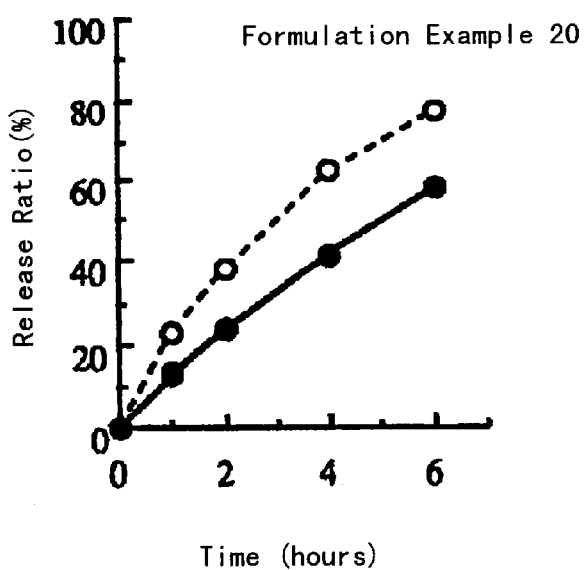
FIG. 20 is a graph showing the release profiles of the drug from the tablet obtained in Formulation Example 20.
Figure 21:
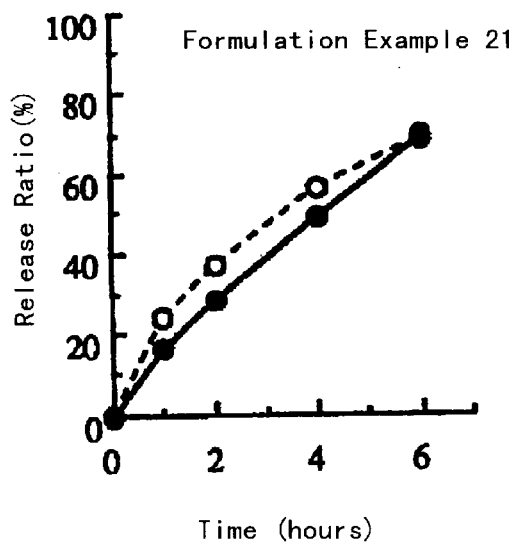
FIG. 21 is a graph showing the release profiles of the drug from the tablet obtained in Formulation Example 21.
Figure 22:
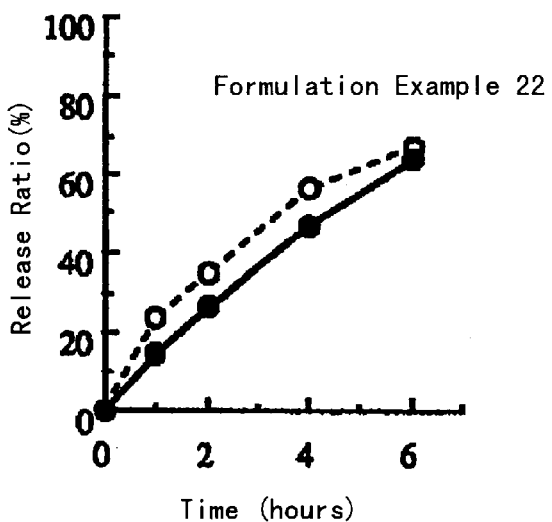
FIG. 22 is a graph showing the release profiles of the drug from the tablet obtained in Formulation Example 22.
Figure 23:
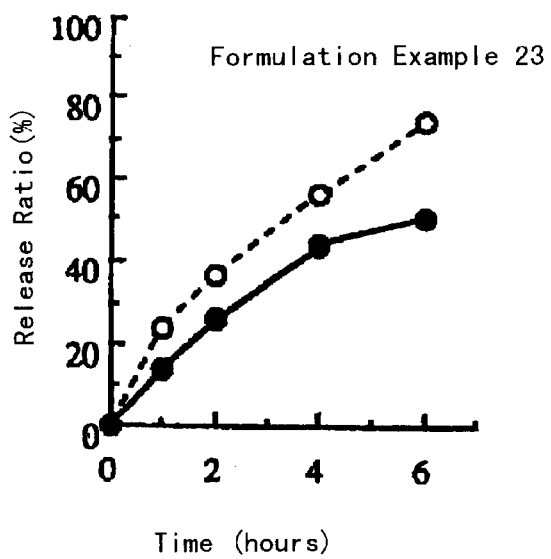
FIG. 23 is a graph showing the release profiles of the drug from the tablet obtained in Formulation Example 23.
Figure 24:
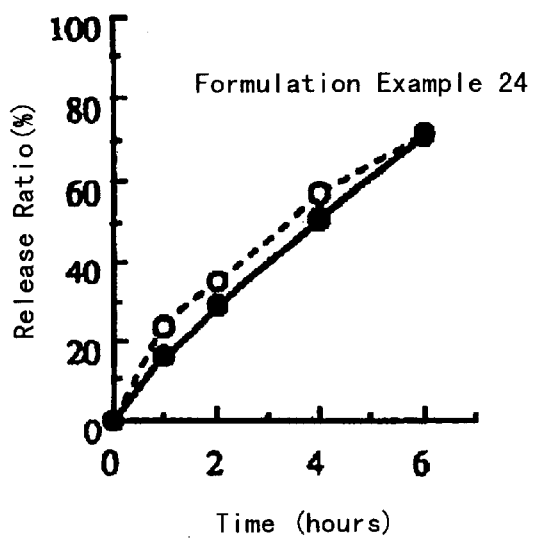
FIG. 24 is a graph showing the release profiles of the drug from the tablet obtained in Formulation Example 24.
Figure 25:
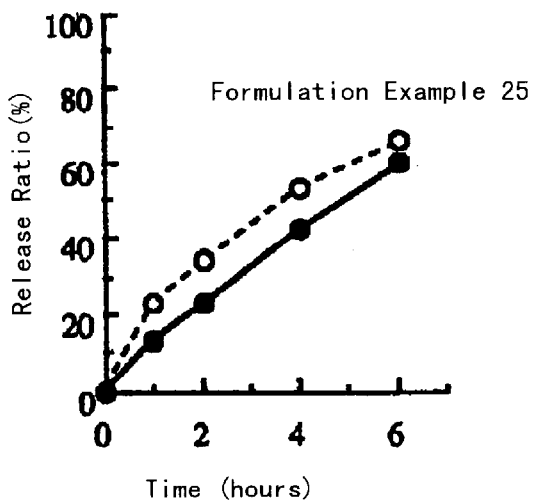
FIG. 25 is a graph showing the release profiles of the drug from the tablet obtained in Formulation Example 25.
Figure 26:
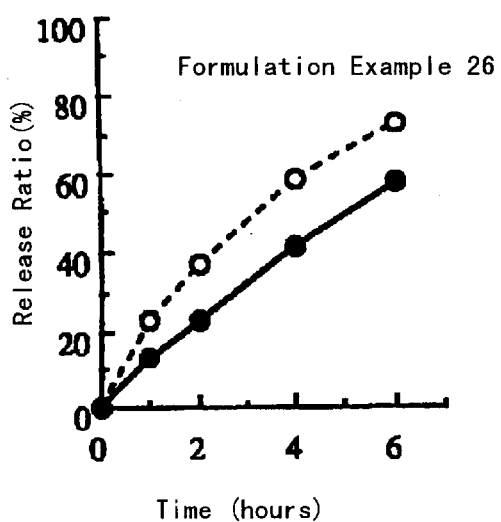
FIG. 26 is a graph showing the release profiles of the drug from the tablet obtained in Formulation Example 26.
Figure 27:
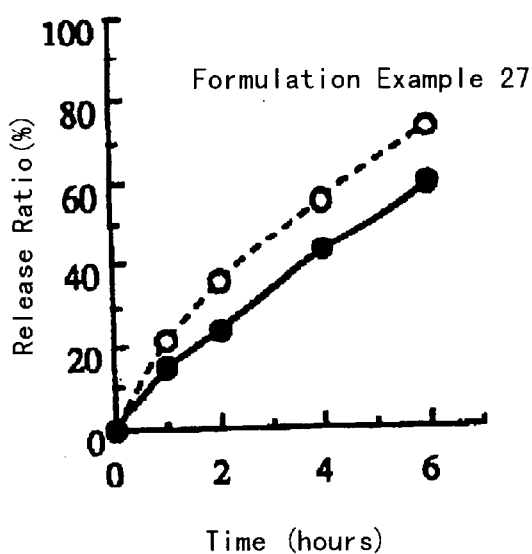
FIG. 27 is a graph showing the release profiles of the drug from the tablet obtained in Formulation Example 27.
Figure 28:
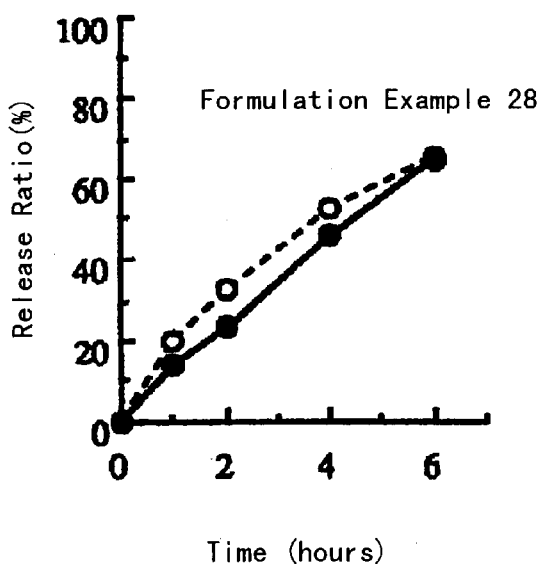
FIG. 28 is a graph showing the release profiles of the drug from the tablet obtained in Formulation Example 28.
Figure 29:
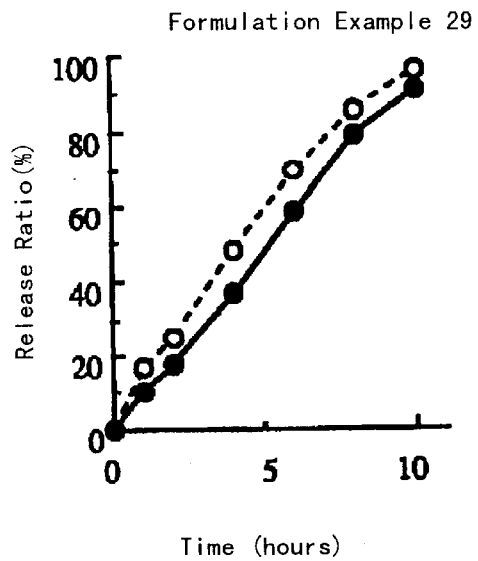
FIG. 29 is a graph showing the release profiles of the drug from the tablet obtained in Formulation Example 29.
Figure 30:
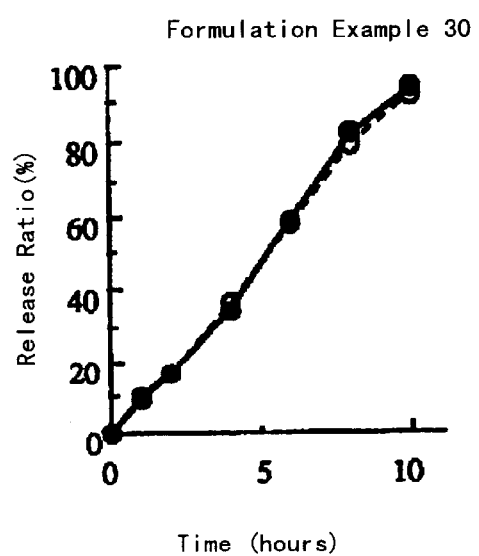
FIG. 30 is a graph showing the release profiles of the drug from the tablet obtained in Formulation Example 30.
Figure 31:
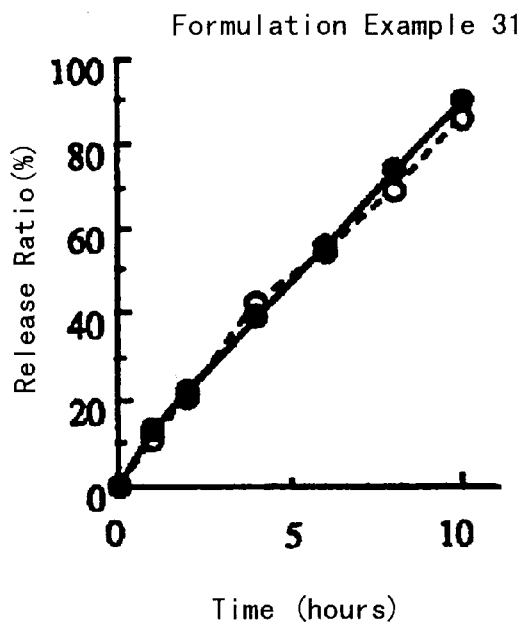
FIG. 31 is a graph showing the release profiles of the drug from the tablet obtained in Formulation Example 31.
Figure 32:
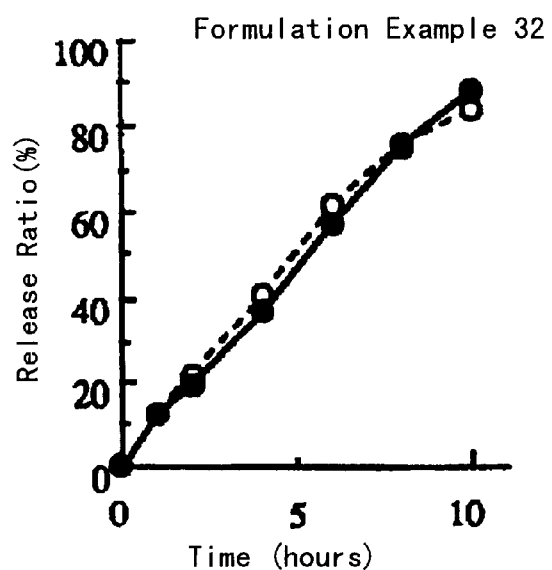
FIG. 32 is a graph showing the release profiles of the drug from the tablet obtained in Formulation Example 32.
Figure 33:
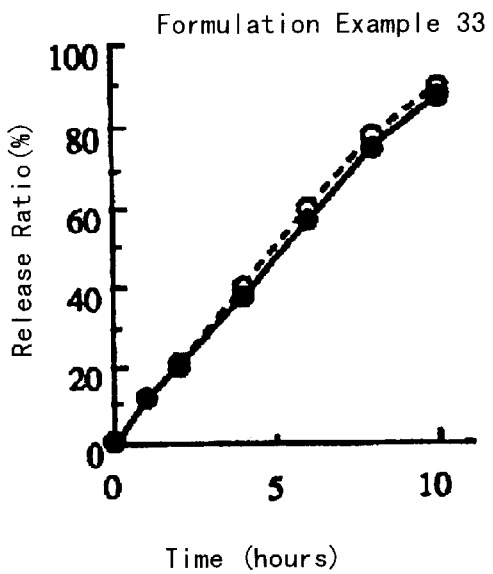
FIG. 33 is a graph showing the release-profiles of the drug from the tablet obtained in Formulation Example 33.
Figure 34:
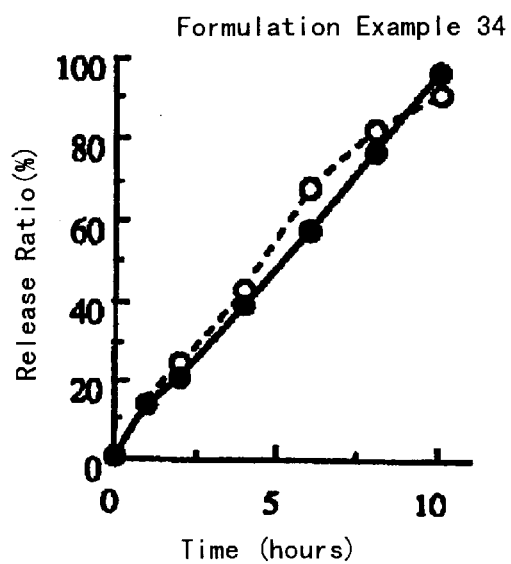
FIG. 34 is a graph showing the release profiles of the drug from the tablet obtained in Formulation Example 34.
Figure 35:
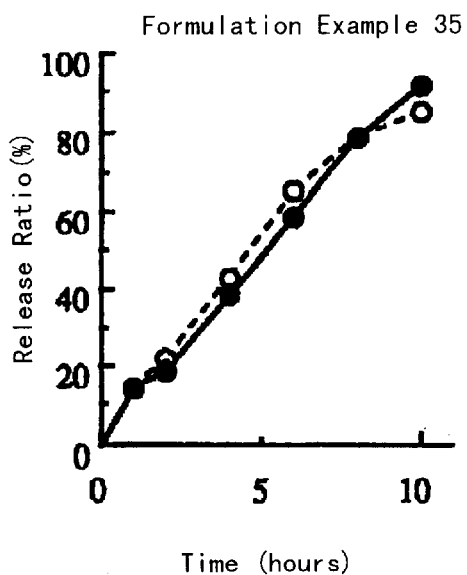
FIG. 35 is a graph showing the release profiles of the drug from the tablet obtained in Formulation Example 35.
Figure 36:
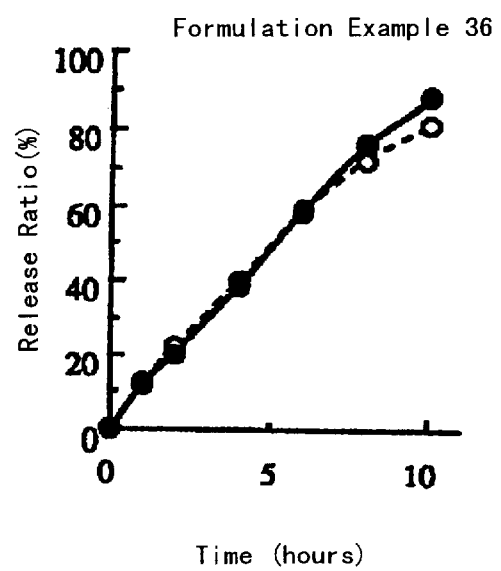
FIG. 36 is a graph showing the release profiles of the drug from the tablet obtained in Formulation Example 36.

As mentioned above, the preparation according to the present invention contains one or more PGI derivatives as an active ingredient. Examples of the PGI derivatives include PGI1 derivatives, $PGI_2$ derivatives and $PGI_3$ derivatives as well as salts and esters thereof. Preferably, $PGI_2$ derivatives as well as salts and esters thereof may be employed. More preferably, the compounds represented by the following formula (I) as well as salts and esters thereof may be employed.

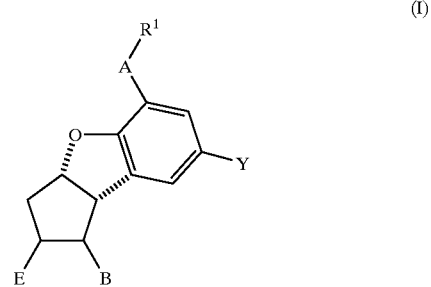

(I)

{wherein $R^1$ is (A) $COOR^2$ wherein $R^2$ is 1) hydrogen or a pharmaceutically acceptable cation,
2) $C_1$–$C_{12}$ straight alkyl or $C_3$–$C_{14}$ branched alkyl,
3) —Z—$R^3$ wherein Z is a valence bond or straight or branched alkylene represented by $C_tH_{2t}$, wherein t is an integer of 1–6, $R^3$ is $C_3$–$C_{12}$ cycloalkyl or $C_3$–$C_{12}$ cycloalkyl substituted with 1 to 3 $R^4$ wherein $R^4$ is hydrogen or $C_1$–$C_5$ alkyl, 4) —$(CH_2CH_2O)_n CH_3$ wherein n is an integer of 1–5, 5) —Z—$Ar^1$ wherein Z represents the same meaning as described above, $Ar^1$ is phenyl, α-naphthyl, β-naphthyl, 2-pyridyl, 3-pyridyl, 4-pyridyl, α-furyl, β-furyl, α-thienyl, β-thienyl or substituted phenyl (wherein the substituent is at least one selected from the group consisting of chlorine, bromine, fluorine, iodine, trifluoromethyl, $C_1$–$C_4$ alkyl, nitro, cyano, methoxy, phenyl, phenoxy, p-acetamidobenzamide, —CH=N—NH—C(=O)—$NH_2$, —NH—C(=O)—Ph, —NH—C(=O)—$CH_3$ and —NH—C(=O)—$NH_2$—), 6) —$C_tH_{2t}COOR^4$ wherein $C_tH_{2t}$ and $R^4$ represent the same meanings as described above, 7) —C$_r$H$_{2r}$N(R$^4$)$_2$
   wherein C$_r$H$_{2r}$ and R$^4$ represent the same meanings as described above,
8) —CH(R$^5$)—C(=O)—R$^6$
   wherein R$^5$ is hydrogen or benzoyl, R$^6$ is phenyl, p-bromophenyl, p-chlorophenyl, p-biphenyl, p-nitrophenyl, p-benzamidephenyl or 2-naphthyl,
9) —C$_p$H$_{2p}$—W—R$^7$
   wherein W is —CH=CH—, —CH=CR— or —C≡C—, R$^7$ is hydrogen, C$_1$–C$_{30}$ straight or branched alkyl or aralkyl, p is an integer of 1–5, or
10) —CH(CH$_2$OR$^8$)$_2$
    wherein R$^8$ is C$_1$–C$_{30}$ alkyl or acyl
(B) —CH$_2$OH
(C) —C(=O)N(R$^9$)$_2$
    wherein R$^9$ is hydrogen, C$_1$–C$_{12}$ straight alkyl, C$_3$–C$_{12}$ branched alkyl, C$_3$–C$_{12}$ cycloalkyl, C$_4$–C$_{13}$ cycloalkylalylene, phenyl, substituted phenyl (wherein the definition of the substituents are the same as (A)5) described above), C$_7$–C$_{12}$ aralkyl or —SO$_2$R$^{10}$, wherein R$^{10}$ is C$_1$–C$_{10}$ alkyl, C$_3$–C$_{12}$ cycloalkyl, phenyl, substituted phenyl (wherein the definition of the substituents are the same as (A)5) described above) or C$_7$–C$_{12}$ aralkyl, with the proviso that although the two R$^9$ may be the same or different, when one is —SO$_2$R$^{10}$, the other R$^9$ is not —SO$_2$R$^{10}$, or
(D) —CH$_2$OTHP (wherein THP represents tetrahydropyranyl),
A is
   1) —(CH$_2$)$_m$—
   2) —CH=CH—CH$_2$—
   3) —CH$_2$—CH=CH—
   4) —CH$_2$—O—CH$_2$—
   5) —CH=CH—
   6) —O—CH$_2$— or
   7) —C≡C—
   wherein m is an integer of 1 to 3,
Y is hydrogen, C$_1$–C$_4$ alkyl, chlorine, bromine, fluorine, formyl, methoxy or nitro,
B is —X—C(R$^{11}$)(R$^{12}$)OR$^{13}$
   wherein R$^{11}$ is hydrogen or C$_1$–C$_4$ alkyl, R$^{13}$ is hydrogen, C$_1$–C$_{14}$ acyl, C$_6$–C$_{15}$ aroyl, tetrahydropyranyl, tetrahydrofuranyl, 1-ethoxyethyl or t-butyl,
X is
   1) —CH$_2$—CH$_2$—
   2) —CH=CH—, or
R$^{12}$ is
   1) C$_1$–C$_{12}$ straight alkyl or C$_3$–C$_{14}$ branched alkyl,
   2) —Z—Ar$^2$
      wherein Z represents the same meaning as described above, Ar$^2$ represents phenyl, α-naphthyl, β-naphthyl or phenyl substituted with at least one selected from the group consisting of chlorine, bromine, fluorine, iodine, trifluoromethyl, C$_1$–C$_4$ alkyl, nitro, cyano, methoxy, phenyl and phenoxy,
   3) —C$_t$H$_{2t}$OR$^{14}$
      wherein C$_t$H$_{2t}$ represents the same meaning as described above, R$^{14}$ is C$_1$–C$_6$ straight alkyl, C$_3$–C$_6$ branched alkyl, phenyl or substituted phenyl substituted with at least one selected from the group consisting of chlorine, bromine, fluorine, iodine, trifluoromethyl, C$_1$–C$_4$ alkyl, nitro, cyano, methoxy, phenyl and phenoxy, cyclopentyl, cyclohexyl, or cyclopentyl or cyclohexyl substituted with 1 to 4 C$_1$–C$_4$ straight alkyl,
   4) —Z—R$^3$
      wherein Z and R$^3$ represent the same meanings as described above,
   5) —C$_r$H$_{2r}$—CH=C(R$^{15}$)R$^{16}$
      wherein C$_r$H$_{2r}$ represents the same meaning as described above, R$^{15}$ and R$^{16}$ independently represent hydrogen, methyl, ethyl, propyl or butyl, or
   6) —C$_u$H$_{2u}$—C≡C—R$^{17}$
      wherein u is an integer of 1–7, C$_u$H$_{2u}$ is straight or branched alkylene, R$^{17}$ is C$_1$–C$_6$ straight alkyl,
E is hydrogen or —OR$^{18}$
   wherein R$^{18}$ is C$_1$–C$_{12}$ acyl, C$_7$–C$_{15}$ aroyl or R$^2$ (wherein R$^2$ represents the same meaning as described above),
the formula represents d-isomer, l-isomer and racemic mixture).

Specific preferred examples of the PGI derivatives include beraprost represented by the following formula:

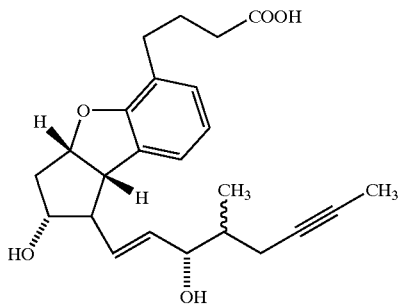

iloprost, clinprost, ataprost, ciprostene, naxaprostene, taprostene, cicaprost, pimilprost, CH-169, SM-10902 and CS570 as well as salts and esters thereof, although the PGI derivatives are not restricted thereto. As the salts, any salt may be employed as long as it is pharmaceutically acceptable. Although the esters are not restricted, alkyl esters are preferred.

The PGI derivatives which may be employed in the present invention may be produced by known methods. For example, the compounds represented by the formula (I) may be produced by the methods described in Japanese Laid-open Patent Application (Kokai) No. 58-124778 and Japanese Patent Publication (Kokoku) No. 6-62594.

As for the amount of the pharmacologically active component, the content of the pharmacologically active component in one preparation is not restricted as long as therapeutic effect is obtained. However, the present invention is especially useful for formulations containing trace amount of drugs for which sustained release keeping good availability is difficult to attain unless the composition according to the present invention is employed. The content of the active component may be, for example, 0.1 to 10,000 μg/preparation, preferably 1 to 1000 μg/preparation, more preferably 10 to 500 μg/preparation. The term "one preparation" herein means the preparation having the dose to be orally administered one time. Although the weight of the one preparation is not restricted, it is usually about 20 to 1000 mg.

In the present invention, the term "release-controlling component" means a substance having a function to change the release rate of the active component by being incorporated in the preparation. How to incorporating the release-controlling component is not restricted. Such a release-controlling component includes so called sustained releasing bases which cause decrease in the release rate; buffer agents for reducing pH change represented by the pH change in the gastrointestinal tract when the active component is released, and for avoiding pH dependence of the releasing rate; solubilizers for improving solubility of the active substance and for stabilizing the release rate by making the diffusion of the active substance be the rate-determining step; and release-accelerators.

In the present invention, in view of stably releasing the above-described trace amount of the pharmacologically active component, a hydrogel base is used as the release-controlling component. In cases where a hydrogel base is used as the release-controlling component, so called zero-order release, that is, the release of which rate fluctuates only to a very small degree, is attained even for a trace amount of active component as small as about 0.1 to 10,000 $\mu$g. As the hydrogel base, known hydrogel bases may be employed. The term "hydrogel" herein used means water-swelling polymers as well as combinations of two or more of these. The hydrogel suited for the purpose of the present invention is made of a polymer which swells to some degree by absorbing water or an aqueous medium upon contact with water or with the aqueous medium. The absorption may be reversible or irreversible, and both of these are within the scope of the present invention. As the hydrogel base, various naturally occurring and synthetic polymeric substances are known. In the present invention, it is preferred to employ a hydrogel base with which the production of the preparation and the ability to control the release may easily be controlled by the molecular weight thereof, which consists essentially of substantially linear polymers that do not have cross-linking structures via covalent bonds, which is free from interaction with the drug and which does not adsorb the drug. Examples of such a hydrogel base include water-soluble polymers such as methyl cellulose, hydroxypropyl cellulose (hereinafter referred to as "HPC" for short), hydroxypropylmethyl cellulose (hereinafter referred to as "HPMC" for short), polyethylene oxide (hereinafter referred to as "PEO" for short), sodium carboxymethyl cellulose, carboxyvinyl polymer, sodium alginate and sodium hyaluronate, as well as mixtures of two or more of these.

Preferred examples of the hydrogel base include HPC, HPMC and PEO as well as mixtures of two or more of these. There are various types of these hydrogel bases depending on the viscosities thereof, and the hydrogel base is appropriately selected depending on the purpose.

The content of the hydrogel base in the preparation may preferably be 10% by weight based on the weight of the preparation to the balance of the prostaglandin I derivative (in cases where the preparation contains a buffer agent, the balance of the prostaglandin I derivative and the buffer agent), more preferably 40 to 95% by weight.

In the present invention, the term "buffer agent" means a substance for reducing pH change represented by the pH change in the gastrointestinal tract when the active component is released, and for avoiding pH dependence of the releasing rate. There are buffer agents which exhibit buffering actions in the acidic region, neutral region or alkaline region, and the buffer agent may be appropriately selected depending on the physicochemical properties of the active component. In the present invention, since most of the PGI derivatives have weakly acidic groups such as carboxyl group, it is preferred to control the dissociation of the weakly acidic group such as carboxyl group of the drug so as to keep the solubility of the drug into the aqueous medium constant, which drug is contained in the hydrogel. Thus, as the buffer agent, organic acids, amino acids and inorganic salts are preferred. Examples of the organic acids include citric acid, succinic acid, fumaric acid, tartaric acid and ascorbic acid as well as salts thereof. Examples of the amino acids include glutamic acid, glutamine, glycine, aspartic acid, alanine and arginine as well as salts thereof. Examples of the inorganic salts include magnesium oxide, zinc oxide, magnesium hydroxide, phosphoric acid and boric acid as well as salts thereof. Mixtures of one or more of the above-mentioned buffer agents are also preferred. As the buffer agent of the sustained release preparation, in order to keep the buffering action for a long time, relatively insoluble buffer agents of which solubilities in water are not more than 15% by weight are preferred. Examples of such a buffer agent include succinic acid, fumaric acid, ascorbic acid, glutamine, glutamic acid, arginine, magnesium oxide, zinc oxide, magnesium hydroxide and boric acid and its salts, as well as mixtures of two or more of these. Acidic buffer agents are more preferred in order to decrease the release rate and sustain the release by inhibiting dissociation of the carboxyl groups of the PGI derivatives. Examples of such a buffer agent include succinic acid, fumaric acid, ascorbic acid, glutamic acid and boric acid and its salts, as well as mixtures of two or more of these. Since such relatively insoluble and acidic buffer agents reduce the pH fluctuation which may accelerate the release of the drug, and reduce the fluctuation of the release rate with time, a constant release rate may be maintained for a long time. Thus, such buffer agents are especially preferred.

The content of the buffer agent may be, for example, 0.1 to 30% by weight based on the weight of one preparation. The content may preferably be 1 to 20% by weight, more preferably 1 to 10% by weight.

To the sustained release preparation according to the present invention, one or more additives such as vehicles, lubricants, binders, stabilizers, solubilizers and the like may be added, which may be used. The additives are not restricted as long as they are pharmaceutically acceptable. Examples of the additives include vehicles such as lactose, saccharose, sucrose, D-mannitol, sorbitol, xylitol, crystalline cellulose, corn starch, gelatin, polyvinylpyrrolidone, dextran, polyethylene glycol (hereinafter referred to as "PEG" for short)-1500, PEG-4000, PEG-6000, PEG-20000 and polyoxyethylenepolyoxypropylene glycol (PEP101, Pluronic); lubricants such as magnesium stearate, calcium stearate and talc; binders such as hydroxypropyl cellulose, hydroxypropylmethyl cellulose, methyl cellulose, stearic acid and propylene glycol; stabilizers such as butylhydroxytoluene, butylhydroxyanisol, ascorbic acid, propyl gallate, dibutylmethyl phenol and sodium thiosulfate; solubilizers such as cyclodextrin, polyethylene-hardened castor oil and polyethylene glycol monostearate. The contents of these additives may appropriately be selected depending on the type and the purpose of the additive.

Although the contents of these additives are not restricted, the contents are usually about 0% by weight to the balance of the prostaglandin I derivative and the hydrogel base (in cases where the preparation contains a buffer agent, the balance of the prostaglandin I derivative, hydrogel base and the buffer agent) based on the weight of one preparation, preferably 5% by weight to the balance of the prostaglandin I derivative and the hydrogel base (in cases where the preparation contains a buffer agent, the balance of the prostaglandin I derivative, hydrogel base and the buffer agent).

Although the combination of the pharmacologically active component, release-controlling component and the buffer agent is not restricted, examples of the combination include beraprost sodium, polyethylene oxide and an acidic and relatively insoluble buffer agent such as fumaric acid or glutamic acid.

Although the dosage form of the sustained release preparation according to the present invention is not restricted, examples thereof include orally administrable dosage forms such as tablet, granules, subtle granules, capsule and syrup.

The use of the sustained release preparation according to the present invention is not restricted, and the preparation may used as, for example, peripheral circulation improvers, antithrombotic drugs, antihypertensive agent, therapeutic agents for cardiac decompensation, various complications of diabetes, digestive ulcer, skin ulcer and for hyperlipidemia, and antiasthmatic.

The preparation according to the present invention is stable, easily administrable and safe, so that stable pharmacological effects are obtained by orally administering the preparation one or two times per day.

EXAMPLES

The present invention will now be described in detail referring to Examples and Comparative Examples thereof. However, the following Examples are presented for the illustration purpose only and should not be interpreted in any restrictive way. In the Examples and Comparative Examples, all "%" are by weight unless otherwise specified.

Example 1

Sustained release preparations were prepared by using the components shown in Tables 1 and 2, and by the Preparation Method 1 or 2 described below.

TABLE 1

| Formulation Example | Active Component Beraprost Sodium | Release-controlling Component Hydrogel Base | Buffer Agent | | Other Vehicle Component | | Lubricant Magnesium Stearate | Total | Preparation Method | FIG. |
|---|---|---|---|---|---|---|---|---|---|---|
| 1 | 0.075% | HPC-H 45% | | 0% | Lactose | 54.625% | 0.3% | 100% | 1 | 1 |
| 2 | 0.075% | HPC-H 45% | Tartaric Acid | 1% | Lactose | 53.625% | 0.3% | 100% | 1 | 2 |
| 3 | 0.075% | HPC-H 45% | Tartaric Acid | 5% | Lactose | 49.625% | 0.3% | 100% | 1 | 3 |
| 4 | 0.075% | HPC-H 45% | Tartaric Acid | 10% | Lactose | 44.625% | 0.3% | 100% | 1 | 4 |
| 5 | 0.075% | HPC-H 45% | Fumaric Acid | 1% | Lactose | 53.625% | 0.3% | 100% | 1 | 5 |
| 6 | 0.075% | HPC-H 45% | Fumaric Acid | 5% | Lactose | 49.625% | 0.3% | 100% | 1 | 6 |
| 7 | 0.075% | HPC-H 45% | Fumaric Acid | 10% | Lactose | 44.625% | 0.3% | 100% | 1 | 7 |
| 8 | 0.075% | HPC-H 45% | Citric Acid | 1% | Lactose | 53.625% | 0.3% | 100% | 1 | 8 |
| 9 | 0.075% | HPC-H 45% | Citric Acid | 5% | Lactose | 49.625% | 0.3% | 100% | 1 | 9 |
| 10 | 0.075% | HPC-H 45% | Citric Acid | 10% | Lactose | 44.625% | 0.3% | 100% | 1 | 10 |
| 11 | 0.075% | HPC-H 45% | Monopotassium Phosphate | 1% | Lactose | 53.625% | 0.3% | 100% | 1 | 11 |
| 12 | 0.075% | HPC-H 45% | Monopotassium Phosphate | 5% | Lactose | 49.625% | 0.3% | 100% | 1 | 12 |
| 13 | 0.075% | HPC-H 45% | Monopotassium Phosphate | 10% | Lactose | 44.625% | 0.3% | 100% | 1 | 13 |
| 14 | 0.075% | HPC-H 45% | L-ascorbic Acid | 1% | Lactose | 53.625% | 0.3% | 100% | 1 | 14 |
| 15 | 0.075% | HPC-H 45% | L-ascorbic Acid | 5% | Lactose | 49.625% | 0.3% | 100% | 1 | 15 |
| 16 | 0.075% | HPC-H 45% | L-ascorbic Acid | 10% | Lactose | 44.625% | 0.3% | 100% | 1 | 16 |
| 17 | 0.075% | HPC-H 45% | Magnesium Oxide | 1% | Lactose | 53.625% | 0.3% | 100% | 1 | 17 |
| 18 | 0.075% | HPC-H 45% | Magnesium Oxide | 5% | Lactose | 49.625% | 0.3% | 100% | 1 | 18 |
| 19 | 0.075% | HPC-H 45% | Magnesium Oxide | 10% | Lactose | 44.625% | 0.3% | 100% | 1 | 19 |

TABLE 2

| Formulation Example | Active Component Beraprost Sodium | Release-controlling Component Hydrogel Base | | Buffer Agent | | Other Vehicle Component | | Lubricant Magnesium Stearate | Total | Preparation Method | FIG. |
|---|---|---|---|---|---|---|---|---|---|---|---|
| 20 | 0.075% | HPC-H | 45% | Borax | 1% | Lactose | 53.625% | 0.3% | 100% | 1 | 20 |
| 21 | 0.075% | HPC-H | 45% | Borax | 5% | Lactose | 49.625% | 0.3% | 100% | 1 | 21 |
| 22 | 0.075% | HPC-H | 45% | Borax | 10% | Lactose | 44.625% | 0.3% | 100% | 1 | 22 |
| 23 | 0.075% | HPC-H | 45% | Zinc Oxide | 1% | Lactose | 53.625% | 0.3% | 100% | 1 | 23 |
| 24 | 0.075% | HPC-H | 45% | Zinc Oxide | 5% | Lactose | 49.625% | 0.3% | 100% | 1 | 24 |
| 25 | 0.075% | HPC-H | 45% | Zinc Oxide | 10% | Lactose | 44.625% | 0.3% | 100% | 1 | 25 |
| 26 | 0.075% | HPC-H | 45% | Magnesium Hydroxide | 1% | Lactose | 53.625% | 0.3% | 100% | 1 | 26 |
| 27 | 0.075% | HPC-H | 45% | Magnesium Hydroxide | 5% | Lactose | 49.625% | 0.3% | 100% | 1 | 27 |
| 28 | 0.075% | HPC-H | 45% | Magnesium Hydroxide | 10% | Lactose | 44.625% | 0.3% | 100% | 1 | 28 |
| 29 | 0.2% | PEO | 62.5% | | 0% | PEG-6000 | 34.8% | 0.5% | 100% | 2 | 29 |
| 30 | 0.2% | PEO | 59.5% | Fumaric Acid | 5% | PEG-6000 | 34.8% | 0.5% | 100% | 2 | 30 |
| 31 | 0.2% | PEO | 59.5% | Monosodium Fumarate | 5% | PEG-6000 | 34.8% | 0.5% | 100% | 2 | 31 |

TABLE 2-continued

| Formulation Example | Active Component Beraprost Sodium | Release-controlling Component | | Other Vehicle Component | | Lubricant Magnesium Stearate | Total | Preparation Method | FIG. |
|---|---|---|---|---|---|---|---|---|---|
| | | Hydrogel Base | Buffer Agent | | | | | | |
| 32 | 0.2% | PEO 59.5% | L-glutamine | 5% PEG-6000 | 34.8% | 0.5% | 100% | 2 | 32 |
| 33 | 0.2% | PEO 59.5% | L-glutamic Acid | 5% PEG-6000 | 34.8% | 0.5% | 100% | 2 | 33 |
| 34 | 0.2% | PEO 59.5% | Glycine | 5% PEG-6000 | 34.8% | 0.5% | 100% | 2 | 34 |
| 35 | 0.2% | PEO 59.5% | DL-α-alanine | 5% PEG-6000 | 34.8% | 0.5% | 100% | 2 | 35 |
| 36 | 0.2% | PEO 59.5% | Arginine | 5% PEG-6000 | 34.8% | 0.5% | 100% | 2 | 36 |

Preparation Method 1: Beraprost sodium carried on lactose, lactose, a buffer agent and hydroxypropyl cellulose (HPC, H type highly viscose product) are uniformly mixed with a high mixer. The mixture is subjected to compression molding with a roller compactor to form a plate. The plate is then pulverized and granulated with an oscillator. The granules are mixed with 0.3% of magnesium stearate and the resultant is continuously made into tablets to prepare sustained release tablets with a weight of 120 mg/tablet.

Preparation Method 2: Beraprost sodium carried on polyethylene glycol 6000 (PEG-6000), the remaining PEG-6000, a buffer agent and polyethylene oxide (PEO, MW 5,000,000) are uniformly mixed with a high mixer. The resulting mixture is mixed with 0.5% of magnesium stearate and the resultant is continuously made into tablets to prepare sustained release tablets with a weight of 120 mg/tablet.

The sustained release of the sustained release preparations according to the present invention was confirmed by the dissolution testing method as follows:

Dissolution Testing Method: To study the influence by the pH of the medium, release of the drugs was evaluated by the second method (paddle method) of dissolution test in the Japanese Pharmacopoeia using the first fluid (pH 1.2) and the second fluid (pH 6.8) of the disintegration test described in Japanese Pharmacopoeia. That is, a preparation was placed in 500 ml of the testing medium at 37° C. and the medium is stirred with a paddle at 100 rpm, and the release of the drug from the preparation was measured. The concentration of the drug released into the testing medium was measured by HPLC (fluorescence method).

The results are shown in FIGS. 1–36. In the drawings, closed circles show the states of elution in the first solution, and open circles show the states of elution in the second solution.

Comparative Examples 1 and 2

Figure 37:
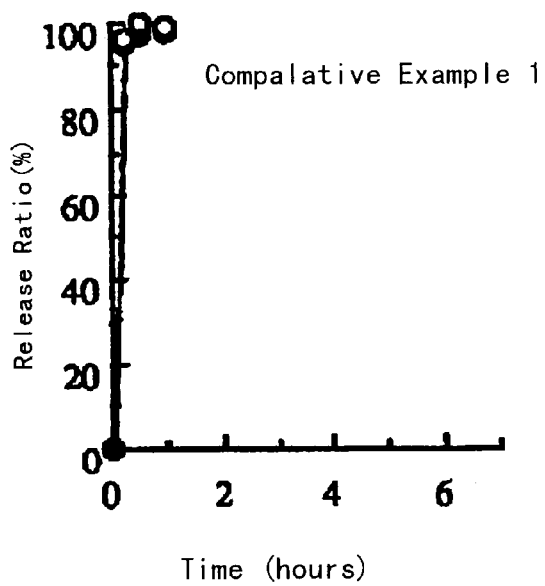
FIG. 37 is a graph showing the release profiles of the drug from the tablet obtained in Comparative Example 1.
Figure 38:
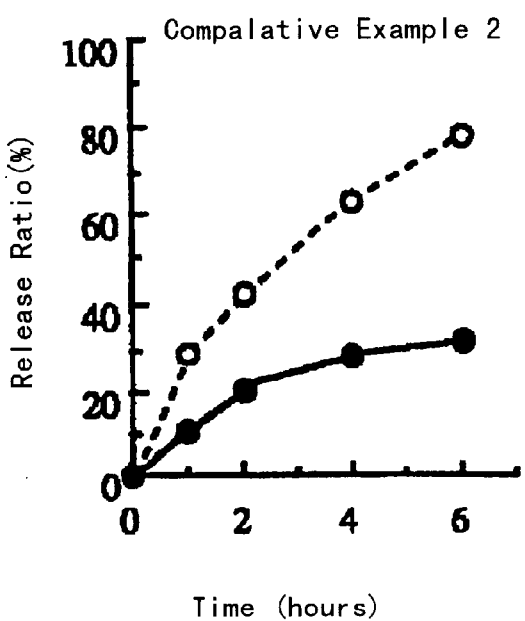
FIG. 38 is a graph showing the release profiles of the drug from the tablet obtained in Comparative Example 2.

As comparative examples, sustained release preparations were prepared using the components shown in Table 3 and by the Preparation Methods 3 and 4, respectively, and dissolution test was carried out as in Example 1. The results of Comparative Example 1 are shown in FIG. 37, and the results of Comparative Example 2 are shown in FIG. 38. In the drawings, closed circles show the release profile in the first fluid, and open circles show the release profile in the second fluid.

TABLE 3

| Comparative Example | Active Component Beraprost Sodium | Release-controlling Component EC | Vehicle Component | | | | Lubricant Magnesium Stearate | Total | Preparation Method | FIG. |
|---|---|---|---|---|---|---|---|---|---|---|
| 1 | 0.075% | 0% | Corn Starch | 40% | Lactose | 54.625% | 0.3% | 100% | 3 | 37 |
| 2 | 0.075% | 60% | PEG-6000 | 10% | Lactose | 29.625% | 0.3% | 100% | 4 | 38 |

Preparation Method 3: Beraprost sodium carried on lactose, lactose and corn starch are uniformly mixed with a high mixer, and aqueous hydroxypropylmethyl cellulose (HPMC) solution is dropped on the mixture, followed by granulating the resulting mixture. The obtained granules were dried and then mixed with 0.3% magnesium stearate, followed by continuously tableting the resulting mixture to obtain quick release tablets with a weight of 120 mg/tablet.

Preparation Method 4: Beraprost sodium carried on lactose, lactose, ethyl cellulose (EC) and PEG-6000 are uniformly mixed with a high mixer. The obtained mixture is mixed with 0.3% magnesium stearate and the resulting mixture is continuously tableted to obtain sustained release tablets with a weight of 120 mg/tablet.

With the Formulation Examples 1–36 employing hydrogel bases, stable and sustained release of beraprost sodium were attained. With any of these preparations, the release ratio after 20 hours was 100%, so that complete release of the drug was observed. On the other hand, in Comparative Example 2, the releasing rate in the first fluid of Japanese Pharmacopoeia drastically decreased with time. With Formulation Examples 2–28 and 30–36 in which a buffer agent was added to the hydrogel base, the release rates in the first fluid (pH 1.2) and in the second fluid (pH 6.8) of Japanese Pharmacopoeia were about the same, so that the release was almost pH-independent. Especially, with Formulation Examples 2, 3, 6, 9, 10, 12, 16 and 30–36, the release patterns in the first and second fluids of Japanese Pharmacopoeia were completely identical, so that ideal preparations which exhibit the zero-order release were obtained.

Example 2

In vivo Absorption Test of Sustained Release Preparation of Beraprost Sodium Using Dogs Although sustained release of the sustained release preparations of beraprost sodium was confirmed in Example 1, to further evaluate the releasing and absorption properties of beraprost sodium in vivo, an oral absorption test using dogs was carried out and the drug concentration in plasma-time profiles were evaluated.

Animal: male beagle dog (administered after fasting), Dose: 900 μg/body (in terms of beraprost sodium)

Measuring Method: EIA method (fluorescence method)

Figure 39:
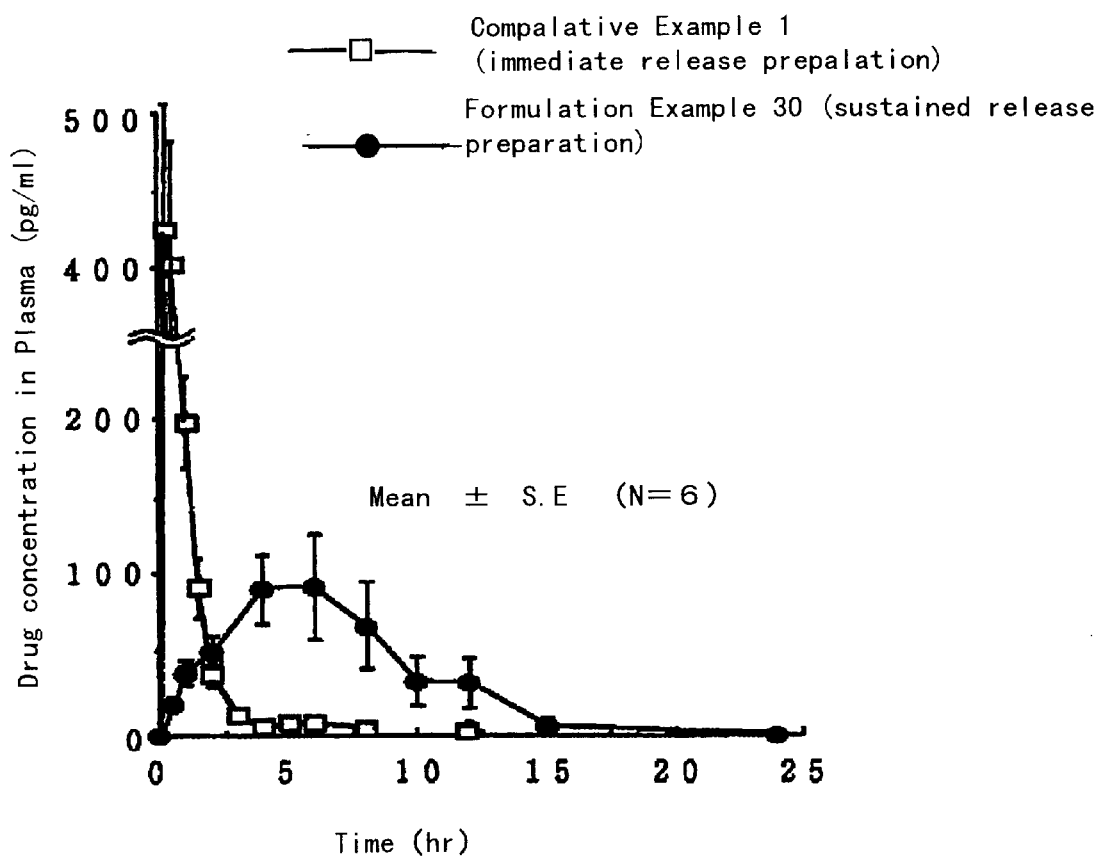
FIG. 39 shows the (drug concentration in plasma)-time profiles obtained by orally administering the immediate release preparation according to Comparative Example 1 or the sustained release tablets according to Formulation Example 30 to dogs.

The results are shown in FIG. 39. By administering the sustained release tablet obtained in Formulation Example 30, the $T_{max}$ was delayed, and the blood level of the drug was sustained for a longer time, and higher bioavailability was obtained when compared with the case where the immediate release tablet obtained in Comparative Example 1 was administered.

As is apparent from the results of the in vitro dissolution tests, the oral sustained release preparations of PGI according to the present invention are very preferred sustained release preparations for the sustained release of the drug in gastrointestinal tract. Further, by adding a buffer agent, pH-independent release was attained. Still further, from the results of the in vivo oral absorption test, it was proved that the blood level of the drug can be maintained for a long time by the preparation. This suggests the sustained expression of pharmacological effects and reduction of side effects. Thus, it is expected that the preparation according to the present invention may be applied to therapies of various diseases as a sustained release preparation with high safety and effectivity.

INDUSTRIAL AVAILABILITY

As described above, the sustained release preparation of prostaglandin I derivatives according to the present invention is a very preferred sustained release preparation for the sustained release of the drug in gastrointestinal tract. It is suggested that the sustained expression of pharmacological effects and reduction of side effects may be attained by the preparation. Thus, it is expected that the preparation may be applied to therapies of various diseases as a sustained release preparation with high safety and effectivity.

What is claimed is:

1. An orally administrable sustained release tablet of prostaglandin I derivative comprising a prostaglandin I derivative, 0.1% by weight to 30% by weight of a buffer and a hydrogel base, said derivative is a prostaglandin I derivative compound represented by the following formula (i) or a salt or ester thereof:

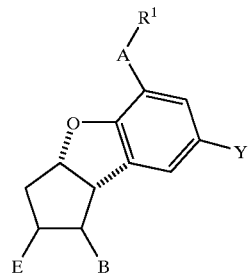

(I)

wherein $R^1$ is
(a) $COOR^2$
  wherein $R^2$ is
  1) hydrogen of a pharmaceutically acceptable cation,
  2) $C_1$–$C_{12}$ straight alkyl or $C_3$–$C_{14}$ branched alkyl,
  3) —Z—$R^3$
    wherein Z is a valence bond or straight or branched alkylene represented by $C_tH_{2t}$, wherein t is an integer of 1–6, $R^3$ is $C_3$–$C_{12}$ cycloalkyl or $C_3$–$C_{12}$ cycloalkyl substituted with 1 to 3 $R^4$ wherein $R^4$ is hydrogen of $C_1$–$C_5$ alkyl,
  4) —$(CH_2CH_2O)_nCH_3$
  5) —Z—$Ar^1$
    wherein Z represents the same meaning as described above, $Ar^1$ is phenyl, α-naphthyl, β-naphthyl, 2-pyridyl, 3-pyridyl, 4-pyridyl, α-furyl, β-furyl, α-thienyl, β-thienyl or substituted phenyl, wherein the substituent is at least one selected from the group consisting of chlorine, bromine, fluorine, iodine, trifluoromethyl, $C_1$–$C_4$-alkyl, nitro, cyano, methoxy, phenyl, phenoxy, p-acetamidobenzamide, —CH=N—NH—C(=O)—$NH_2$, —NH—C(=O)—Ph, —NH—C(=O)—$CH_3$ and —NH—C(=O)—$NH_2$—,
  6) —$C_tH_{2t}COOR^4$
    wherein $C_tH_{2t}$ and $R^4$ represent the same meanings as described above,
  7) —$C_tH_{2t}N(R^4)_2$
    wherein $C_tH_{2t}$ and $R^4$ represent the same meanings as described above,
  8) —$CH(R^5)$—$C(=O)$—$R^6$
    wherein $R^5$ is hydrogen or benzoyl, $R^6$ is phenyl, p-bromophenyl, p-chlorophenyl, p-biphenyl, p-nitrophenyl, p-benzamidephenyl or 2-naphthyl,
  9) —$C_pH_{2p}$—W—$R^7$
    wherein W is —CH=CH—, —CH=$CR^7$— or —C≡C—, $R^7$ is hydrogen, $C_1$–$C_{30}$ straight or branched alkyl or aralkyl, p is an integer of 1–5, or
  10) —$CH(CH_2OR^8)_2$
    wherein $R^8$ is $C_1$–$C_{30}$ alkyl or acyl,
(b) —$CH_2OH$
(c) —$C(=O)N(R^9)_2$
  wherein $R^9$ is hydrogen, $C_1$–$C_{12}$ straight alkyl, $C_3$–$C_{12}$ branched alkyl, $C_3$–$C_{12}$ cycloalkyl, $C_4$–$C_{13}$ cycloalkylalylene, phenyl, substituted phenyl, wherein the definition of the substituents are the same as (a)5) described above, $C_7$–$C_{12}$ aralkyl or —$SO_2R^{10}$, wherein $R^{10}$ is $C_1$–$C_{10}$ alkyl, $C_3$–$C_{12}$ cycloalkyl, phenyl, substituted phenyl, wherein the definition of the substituents are the same as (a)5) described above or $C_7$–$C_{12}$ aralkyl, with the proviso that although the two $R^9$ may be the same or different, when one is —$SO_2R^{10}$, the other is not —$SO_2R^{10}$, or (d) —CH$_2$OTHP
  wherein THP represents tetrahydropyranyl,
A is
  1) —(CH$_2$)$_m$—
  2) —CH=CH—CH$_2$—
  3) —CH$_2$—CH=CH—
  4) —CH$_2$—O—CH$_2$—
  5) —CH=CH—
  6) —O—CH$_2$— or
  7) —C≡C—
    wherein m is an integer of 1 to 3,
Y is hydrogen, C$_1$–C$_4$ alkyl, chlorine, bromine, fluorine, formyl, methoxy or nitro,
B is —X—C(R$^{11}$)(R$^{12}$)OR$^{13}$
  wherein R$^{11}$ is hydrogen or C$_1$–C$_4$ alkyl,
R$^{13}$ is hydrogen, C$_1$–C$_{14}$ acyl, C$_6$–C$_{15}$ aroyl, tetrahydropyranyl, tetrahydrofuranyl, 1-ethoxyethyl or t-butyl,
X is
  1) —CH$_2$—CH$_2$—
  2) —CH=CH—
  3) —C≡C—
R$^{12}$ is
  1) C$_1$–C$_{12}$ straight alkyl, C$_3$–C$_{14}$ branched alkyl,
  2) —Z—Ar$^2$
    wherein Z represents the same meaning as described above, Ar$^2$ represents phenyl, α-naphthyl, β-naphthyl or phenyl substituted with at least one substituent selected from the group consisting of chlorine, bromine, fluorine, iodine, trifluoromethyl, C$_1$–C$_4$-alkyl, nitro, cyano, methoxy, phenyl, phenoxy,
  3) —C$_t$H$_{2t}$COOR$^{14}$
    wherein C$_t$H$_{2t}$ represents the same meaning as described above, R$^{14}$ is C$_1$–C$_6$ straight alkyl, C$_3$–C$_6$ branched alkyl, phenyl or substituted phenyl substituted with at least one substituent selected from the group consisting of chlorine, bromine, fluorine, iodine, trifluoromethyl, C$_1$–C$_4$-alkyl, nitro, cyano, methoxy, phenyl, phenoxy, cyclopentyl, cyclohexyl, or cyclopenyl or cyclohexyl substituted with 1 to 4 C$_1$–C$_4$ straight alkyl,
  4) —Z—R$^3$
    wherein Z and R$^3$ represent the same meanings as described above,
  5) —C$_t$H$_{2t}$—CH=C(R$^{15}$)R$^{16}$
    wherein C$_t$H$_{2t}$ represents the same meaning as described above,
    R$^{15}$ and R$^{16}$ independently represent hydrogen, methyl, ethyl, propyl or butyl, or
  6) —C$_u$H$_{2u}$—C≡C—R$^{17}$
    wherein u is an integer of 1–7,
    C$_u$H$_{2u}$ is a straight or branched alkylene,
    R$^{17}$ is C$_1$–C$_6$ straight alkyl
E is hydrogen or —OR$^{18}$
  wherein R$^{18}$ is C$_1$–C$_{12}$ acyl, C$_7$–C$_{15}$ aroyl or R$^2$
  wherein R$^2$ represents the same meaning as described above,
the formula represents d-isomer, l-isomer and racemic mixture,
  wherein the content of the hydrogel base is 40 to 95% by weight based on the weight of the tablet to the balance of said prostaglandin I derivative, said prostaglandin I derivative being sustainedly released in a patient's gastrointestinal tract.

2. The sustained release tablet of prostaglandin I derivatives according to claim 1, wherein said hydrogel base consists essentially of one selected from the group consisting of methyl cellulose, hydroxypropyl cellulose, hydroxypropylmethyl cellulose, polyethylene oxide, carboxymethyl cellulose, carboxyvinyl polymer, sodium alginate alginate and sodium hyaluronate, or a mixture of two or more of the above.

3. The sustained release tablet of prostaglandin I derivatives according to claim 1, wherein said buffer agent consists essentially of one selected from the group consisting of citric acid, succinic acid, fumaric acid, tartaric acid, ascorbic acid, glutamic acid, glutamine, glycine, aspartic acid, alanine, arginine, magnesium oxide, zinc oxide, magnesium hydroxide, phosphoric acid and boric acid and salts thereof, or a mixture of two or more of the above.

4. The sustained release tablet of prostaglandin I derivatives according to claim 1, which contains 0.1 to 10,000 μg of said prostaglandin derivative based on the weight of the preparation.

* * * * *